United States Patent [19]
Lockhart

[11] Patent Number: 5,154,692
[45] Date of Patent: Oct. 13, 1992

[54] DEVICE FOR USE TO SUPPORT AND IMMOBILIZE DAMAGED TOES

[76] Inventor: Robert D. Lockhart, 107 S. Mary Ave., No. 126, Sunnyvale, Calif. 94086

[21] Appl. No.: 661,586

[22] Filed: Feb. 26, 1991

[51] Int. Cl.$^5$ ................................................ A61F 5/37
[52] U.S. Cl. ........................................ 602/30; 602/5; 128/882
[58] Field of Search ...................... 128/81 R, 882, 869, 128/879, 880, 893, 894; 602/5, 11, 23, 30

[56] References Cited

U.S. PATENT DOCUMENTS

| | | | |
|---|---|---|---|
| 694,762 | 3/1902 | Level | 128/81 R |
| 1,001,161 | 8/1911 | Packard | 128/81 R |
| 2,069,034 | 1/1937 | Hicks | 128/81 R |
| 2,332,473 | 10/1943 | Salander | 128/81 |
| 2,354,770 | 8/1944 | Patterson | 128/81 R |
| 2,461,047 | 2/1949 | Freedman et al. | 128/81 R |
| 2,499,768 | 3/1950 | McGlumphy | 128/81 R |
| 2,510,654 | 6/1950 | Pepin | 36/8.5 |
| 2,585,629 | 2/1952 | Crawford | 128/81 R |
| 2,927,579 | 3/1960 | Braxton | 128/81 |
| 3,110,306 | 11/1963 | Posner | 128/81 R |
| 3,943,922 | 3/1976 | Umeda | 128/81 R |

FOREIGN PATENT DOCUMENTS

| | | |
|---|---|---|
| 537832 | 3/1957 | Canada . |
| 556718 | 4/1958 | Canada . |
| 938266 | of 0000 | Fed. Rep. of Germany . |
| 1039704 | 9/1958 | Fed. Rep. of Germany . |

*Primary Examiner*—Robert A. Hafer
*Assistant Examiner*—Sam Rimell
*Attorney, Agent, or Firm*—Townsend and Townsend

[57] ABSTRACT

A support and immobilizing device for a damaged toe includes a pad having a front edge from which a curved support member projects. The suppport member overlies the damaged toe and is taped to it so that the toe will be supported and immobilized. The device of the present invention can be made for specific toes of the foot and the device will be of specific configurations for the big toe, the little toe, the fourth toe and the second and third toes. Thus, a total of four devices will be made and used for the five toes of each foot; however, the basic construction of the device will always remain the same, such basic construction being the combination of the pad and support member on the top of the foot and toe, respectively.

8 Claims, 2 Drawing Sheets

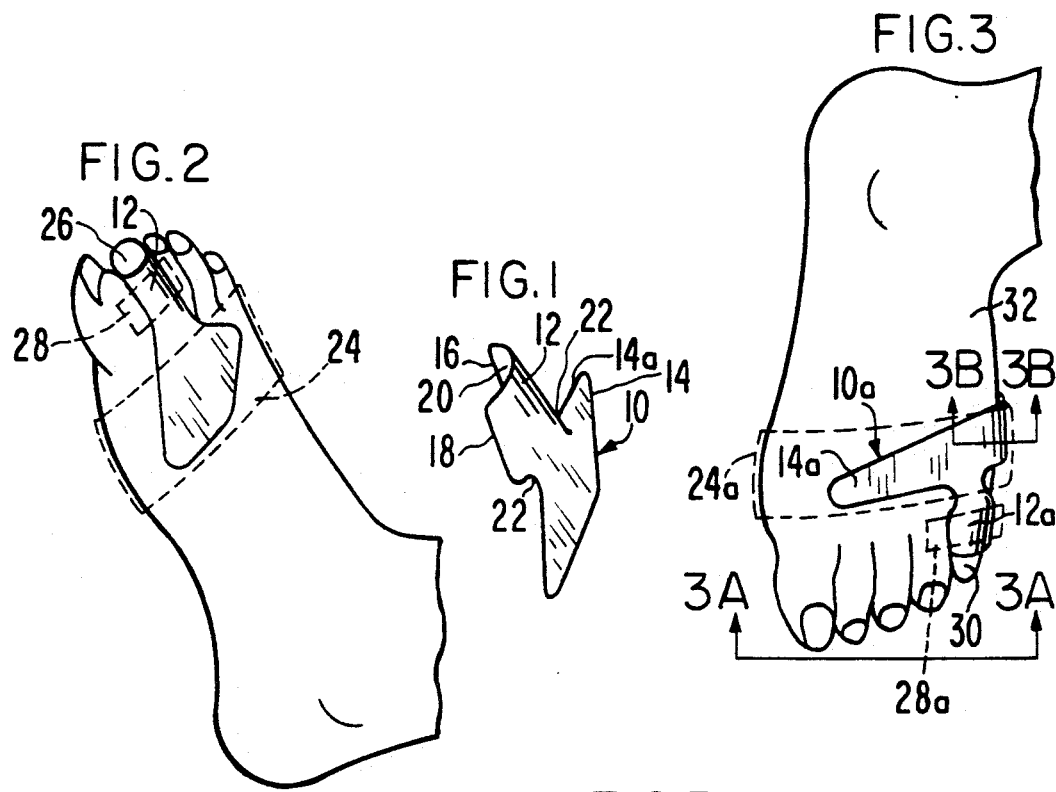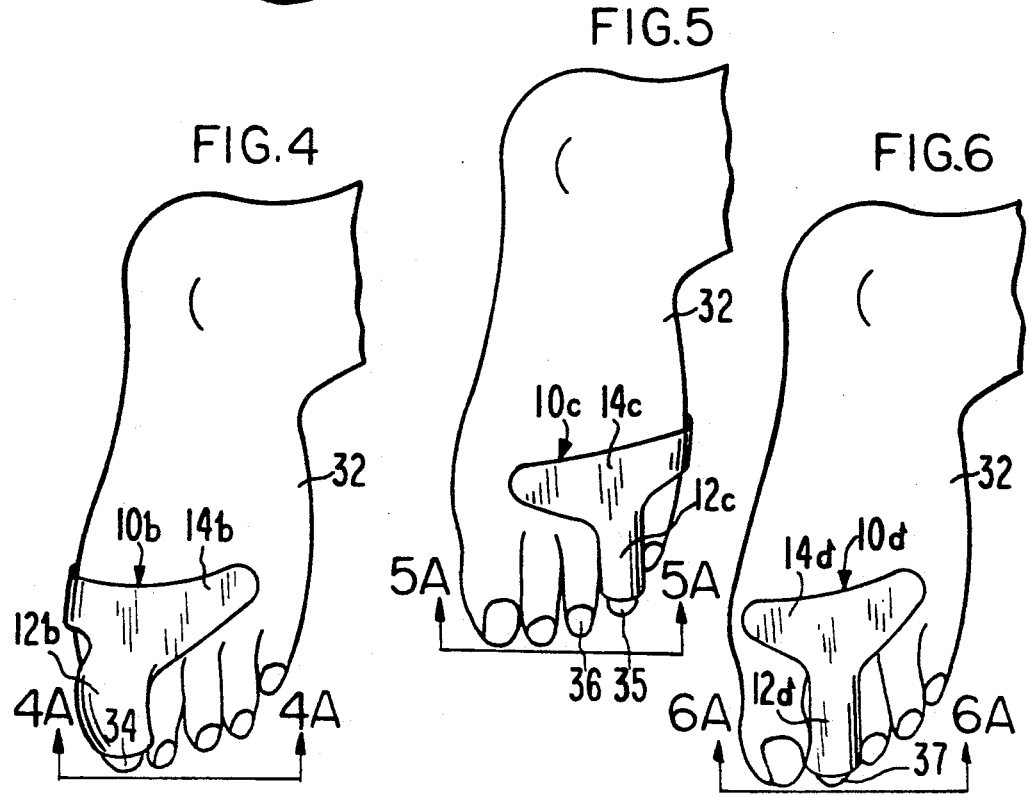

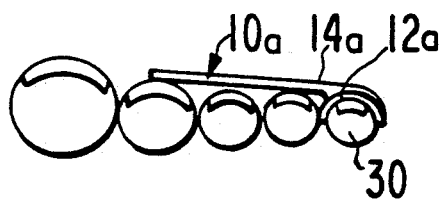
FIG.3A
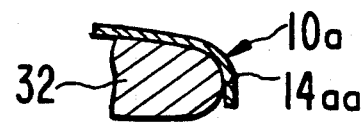
FIG.3B
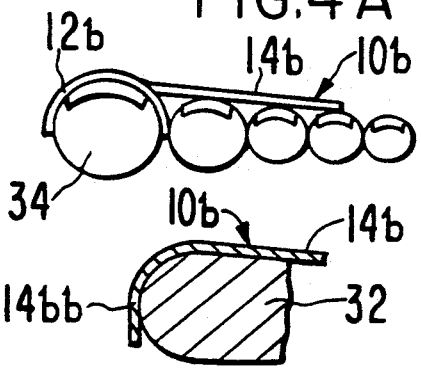
FIG.4A
FIG.4B
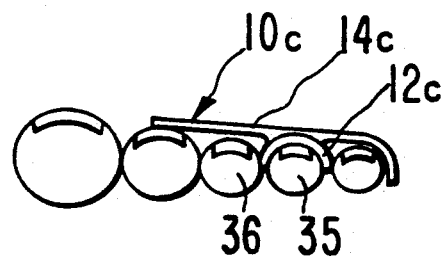
FIG.5A
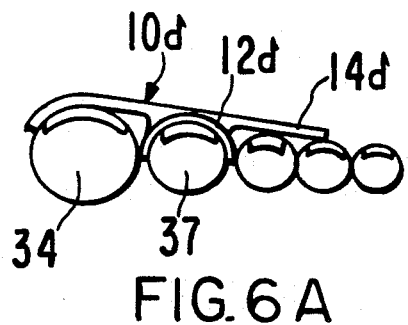
FIG.6A
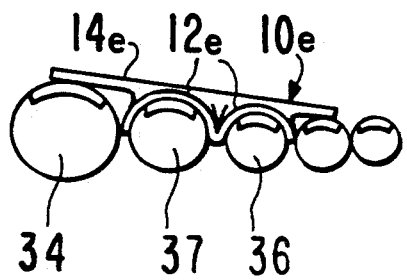
FIG.7

DEVICE FOR USE TO SUPPORT AND IMMOBILIZE DAMAGED TOES

This invention relates to improvements in devices for use in treating the toes of the foot and, more particularly, to a support device for holding a toe in a fixed position during healing of the toe after the toe has been damaged.

BACKGROUND OF THE INVENTION

Toes of the foot are easily damaged and must be immobilized during a healing period. The normal treatment is wrapping the damaged toe with tape and wearing an orthopedic shoe.

Devices have been constructed to immobilize toes during recovery, but most of these devices have been placed on the bottom of the wearer's foot. A tape or other wrapping material wound about the pad keeps the pad below the foot. However, this pad must be sufficiently thick to support the weight of the person. Because it is thick, the pad is uncomfortable as the person takes a step. Moreover, since the pad is on the bottom of the foot, flexing of the bottom of the foot causes flexing of the pad which adds to the discomfort due to the pad. Thus, a pad of conventional design is difficult to fit and, even if were fitted in what might be considered a proper manner, the pad still causes discomfort to the foot. Over long periods of time, the conventional pad creates an environment in which healing of a damaged toe takes longer than is necessary. Therefore, the normal device for immobilizing damaged toes is simply to wrap them with tape.

Because of the foregoing drawbacks, a need exists for improvements in devices for supporting and immobilizing a toe in a manner such as to enhance the healing of the toe after it has been damaged. The present invention satisfies this need.

SUMMARY OF THE INVENTION

The present invention is directed to an improved support and immobilizing device for a damaged toe or several toes in which the device includes a pad which engages the top of the foot and having a front edge from which a curved support member projects. The support member overlies the damaged toe and is taped to it so that the toe will be supported and immobilized. The support member projects forwardly from the front edge of the pad intermediate the ends of the pad. The support member is integral with the pad so that the device forms a one-piece construction of plastic or metal. If formed of plastic, the device can be molded in a simple process. Moreover, if the device is molded, it can be made to be substantially complemental to an outer surface portion of the top of the foot and an outer surface portion of the top of the toe to be supported and immobilized.

The support member on the forward edge of the pad has a downwardly facing concave inner surface to present a recess for receiving the toe to be supported and immobilized. Once the device is in place, the pad is fixed or coupled to the top of the foot by a tape or other wrapping material. Likewise, the toe is fixed to the support member by a tape or other wrapping. Fixing the device to the top of the foot is a critical feature. The reason for this is that, since the device does not support the person's weight, it can be made thinner in size. The device will, therefore, not cause discomfort to the wearer, such as occurs in the case of conventional pads which are relatively thick and are worn on the bottom of the foot. It will also provide more support and protection than bandages provide. Also, by placing the pad on the top of the foot, the wearer does not experience any discomfort because the flexing of the top of the foot is much less than the flexing of the bottom of the foot. The device of the present invention is thereby greatly superior to conventional devices for supporting and immobilizing a toe.

The device of the present invention can be made for specific toes of the foot and the device will be of specific configurations for the big toe, the little toe, the fourth toe and the second and third toes. Thus, a total of four devices will be made and used for the five toes of each foot; however, the basic construction of the device will always remain the same, such basic construction being the combination of the pad and support member on the top of the foot and toe, respectively.

The primary object of the present invention is to provide an improved toe supporting and immobilizing device which avoids the problems of conventional devices for treating damaged toes to thereby provide a greater amount of comfort to the user while enhancing the healing of a damaged toe.

Another object of the present invention is to provide a supporting and immobilizing device for a toe of the foot wherein the device is formed of a pad and a support member which are applied to the upper part of a foot to avoid the problems associated with conventional devices applied to the bottom surface of the foot, and to provide more support than bandaging does.

Other objects of the present invention will become apparent as the following specification progresses, reference being had to the accompanying drawings for an illustration of the invention.

BRIEF DESCRIPTION OF THE DRAWINGS

FIG. 1 is a perspective view of a toe support of the present invention;

FIG. 2 is a perspective view of a foot showing the way in which the support device can be mounted on the right foot for supporting the second toe FIG. 3 is a top plan view of the left foot, showing the way in which the device can be used to support the little toe of the foot;

FIG. 3A is a front elevational view looking in the direction of line 3A—3A of FIG. 3;

FIG. 3B is a cross sectional view taken along line 3B—3B of FIG. 3;

FIG. 4 is a view similar to FIG. 3 but showing the device for supporting the big toe of the left foot;

FIG. 4A is a front elevational view looking in the direction of line 4A—4A of FIG. 4;

FIG. 4B is a cross sectional view taken along line 4B—4B of FIG. 4;

FIGS. 5 and 6 are views similar to FIGS. 3 and 4 but showing the device in place for supporting the third and second toes, respectively, of the left foot;

FIGS. 5A and 6A are front elevational views taken along lines 5A—5A and 6A—6A of FIGS. 5 and 6, respectively; and FIG. 7 is a view similar to FIG. 3A but showing the device when the same is adapted to support and immobilize a pair of adjacent toes, namely the second and third toes of the left foot.

DETAILED DESCRIPTION OF THE DRAWINGS

The toe support and immobilizing device of the present invention is broadly denoted by the numeral 10 and includes a toe support member 12 integral with a pad 14 so as to form a one-piece construction for the device. The support member 12 and pad 14 can be of any suitable material, such as plastic or metal. If formed of plastic, device 10 can be molded in a simple molding process.

Device 10 can vary in dimension so that it can fit the toes of persons of different sizes. Moreover, the device 10 will vary in size and shape to accommodate a particular toe of the foot; thus, the device will typically have the shape of FIG. 3 when the small toe is to be supported. The device will take the shape of Fig. 4 when the big toe is to be supported; the device will take the shape of FIG. 5 if the fourth toe is to be supported; and the device will take the shape of FIG. 6 if the second or third toe is to be supported. FIG. 7 shows a device having a support member which overlies and supports a pair of adjacent toes, such as the second and third toe of the left foot.

Generally, the pad of the present invention is flat although it could be slightly inclined and even slightly V-shaped so as to substantially engage the upper surface of the foot. The pad is elongated so that the toe support member 12 in FIG. 1 extends forwardly from the front edge 14a of pad 14 with member 12 being intermediate the ends of the pad as shown in FIG. 1. The length of member 12 is substantially equal to the length of the toe adjacent thereto. For instance, as shown in FIG. 3, the length the support member is substantially equal to the length of the small toe.

Member 12 is transversely semicircular and has a recess which is defined by a pair of lower edges 16 and 18 (FIG. 1). The recess further has an open bottom through which a toe passes as the toe moves into the recess. Support member 12 has a concave inner surface 20 which typically rests upon or overlies the adjacent toe. The rear end of the support member 12 is slightly cut away, such as at locations 22 near the pad 14 and these cutaway portions permit the toe to be received in the recess of the support member 12 without interference with the toe and without causing discomfort to the toe or the region of the foot from which the toe projects forwardly.

When a device 10 is coupled to the foot, such as in the case of the device 10 on the foot of FIG. 2, the pad is coupled or attached to the foot by a tape 24 or other wrapping material such that the pad is rendered fixed to the foot. The second toe 26 which is beneath the support member 12 is coupled to the support member by a tape 28 which is shown in dashed lines in FIG. 2 as extending laterally from the sides of the member 12, but it is to be understood that the tape 28 is wrapped around the member 12 and toe 26 so as to couple the toe to the member. Thus, the toe 26 is fixed to the device 10, and the device stabilizes the toe and immobilizes it so that the toe can heal more quickly.

Fixing the device 10 to the top of the foot is critical because the device does not support the weight of the person; thus, the device can be much thinner than conventional pads which engage the bottom of the foot. Moreover, flexing of the top of the foot while walking is much less than flexing of the bottom of the foot; thus, the top of the foot is much superior to the bottom of the foot as a base for immobilizing the toes. In summary, device 10 provides a better toe support than conventional pads. Thus, the device 10 provides a comfortable support for the toe and allows the toe to heal quickly while the toe is continuously in a fixed position with reference to the foot.

As to the shapes and sizes of the device 10 for use with different toes, reference is had to FIGS. 3–6 wherein FIG. 3 shows a device 10a having a pad 14a and a support member 12a which is substantially of a length equal to the length of the small toe 30. Pad 14a is essentially wedged-shaped and has a vertical portion 14b as shown in FIG. 3B, portion 14b extending along the sides of the foot 32 so as to fix device 10a in place and prevent it from moving laterally to the left when viewing FIG. 3. FIG. 3A shows device 10a with support member 12a overlying the small toe 30.

FIG. 4 shows foot 32 with a device 10b having a pad 14b and a support member 12b. FIG. 4 shows, with FIG. 4A, that pad 14b overlies at least two of the toes adjacent to the big toe 34. FIG. 4B shows a vertical device 10b.

FIG. 5 shows a device 10c having a pad 14c and a support member 12c integral with pad 14c, the support member 12c being used to overlie the fourth toe 35 adjacent to the third toe 36. Pad 14c has a vertical portion, such as portion 14aa of FIG. 3B, such vertical portion of pad 14c being used to stabilize device 10c when the device is mounted on foot 32 of FIG. 5.

FIG. 6 shows foot 32 with device 10d on the foot, device 10d including a pad 14d and a support member 12d for covering the second toe 37. FIG. 6A shows support member 12d overlying the second toe 37 adjacent to first toe 34, the pad covering toe 34 as well as the third and fourth toes, as shown in FIG. 6A.

FIG. 7 shows a support device 10e having a pair of adjacent, side-by-side support member 12e on a pad 14e. The pad overlies the big toe 34 and the second, third and fourth toes with the two support members 12e overlying, supporting and immobilizing respective second and third toes 37 and 36, respectively. It is to be understood that when the device 10 is in place on the foot, the device is held in place by a tape or other wrapping material, such as tape 24 of FIG. 2 or a tape 24a of FIG. 3. Similarly, tape 28 of FIG. 2 and tape 28a of FIG. 3 are used to couple the toe to be supported with the corresponding support members.

I claim:

1. A device for supporting and immobilizing the toe of a foot comprising:
    a rigid unitary support member having first, second and third portions;
    the first portion being generally triangular in shape and having a lower surface for placement on the adjacent upper surface of the foot, the second portion being generally semicircular in cross section for placement on an upper portion of a toe, the second portion being generally equal in length to said toe, the third portion connecting said first and second portions, the third portion having a pair of recessed sides to prevent interfering contact with the portion of said toe adjacent to said foot, and a flexible member of wrapping material for wrapping around one of the portions for attaching the support member to the foot.

2. In a device as set forth in claim 1, wherein said support member includes a pair of extensions which are generally parallel with each other and are secured to the first portion and extend forwardly therefrom, the extensions being adapted to overly respective toes and to be coupled therewith.

3. In a device a set forth in claim 1, wherein the first portion has a length sufficient to cause at least one side of the first portion to overly a pair of adjacent toes adjacent to the support member.

4. In a device as set forth in claim 1, wherein the first portion has a vertical portion for extending along the side of the foot as a generally horizontal portion of the first portion engages the upper surface of the foot and when the second portion overlies the toe adjacent to the side of the foot.

5. In a device as set forth in claim 1, wherein the second portion includes a concave inner surface defining a recess having an open bottom for receiving the toe to be supported and immobilized, and including a length of a wrapping material wound on the support member and adapted to be wound on the toe in the recess of the support member.

6. In a device as set forth in claim 5, wherein said concave surface is substantially transversely semicircular.

7. In a device as set forth in claim 5, wherein the support member has a pair of spaced lower, forwardly extending side marginal edges defining the entrance to the lower end of the support member for receiving the toe to be supported and immobilized.

8. In a device as set forth in claim 7, wherein the first portion has a vertical portion adapted to extend along an adjacent side of the foot near said one end of the first portion to stabilize the first portion on the foot when the support member overlies the toe near said one end of the first portion.

* * * * *